United States Patent [19]

Dorrance

[11] 4,327,239

[45] Apr. 27, 1982

[54] METHOD FOR PRODUCING HYDROCARBONS AND OXYGEN FROM CARBON DIOXIDE AND WATER

[75] Inventor: William H. Dorrance, Ann Arbor, Mich.

[73] Assignee: Organization Control Services, Inc., Ann Arbor, Mich.

[21] Appl. No.: 238,487

[22] Filed: Feb. 26, 1981

[51] Int. Cl.$^3$ .............................................. C07C 1/12
[52] U.S. Cl. .................................... 585/733; 585/638
[58] Field of Search ............................... 585/733, 638

[56] References Cited

U.S. PATENT DOCUMENTS 4,197,421  4/1980  Steinberg ........................ 585/733
4,278,650  7/1981  Dorrance ........................ 423/579

Primary Examiner—Robert V. Hines
Attorney, Agent, or Firm—Olsen and Stephenson

[57] ABSTRACT

Water is fed into a high temperature pressurized vessel containing hydrated zeolite material loaded with a metal cation in its highest oxidation state. The high temperature causes an endothermic redox reaction to occur that produces oxygen gas and, as a solid reaction product, hydrated zeolite material containing the metal cation in a lower oxidation state and protons. The solid reaction product is passed through a heat exchanger, where it is cooled, and then into a second pressurized reaction vessel at low temperature. Carbon dioxide is fed into the low temperature reaction vessel whereby an exothermic redox reaction occurs that produces a mixture of hydrocarbons and water and that oxidizes the cation back to its highest oxidation state. The oxidized-cation containing hydrated zeolite material generated in the second reaction vessel is passed through the formentioned heat exchanger, where it is heated, and then passed back to the first reaction vessel for recycling. Pressurization is employed in the reaction vessels to prevent dehydration and this, together with the use of the heat exchanger, provides high process thermal efficiency.

10 Claims, 1 Drawing Figure

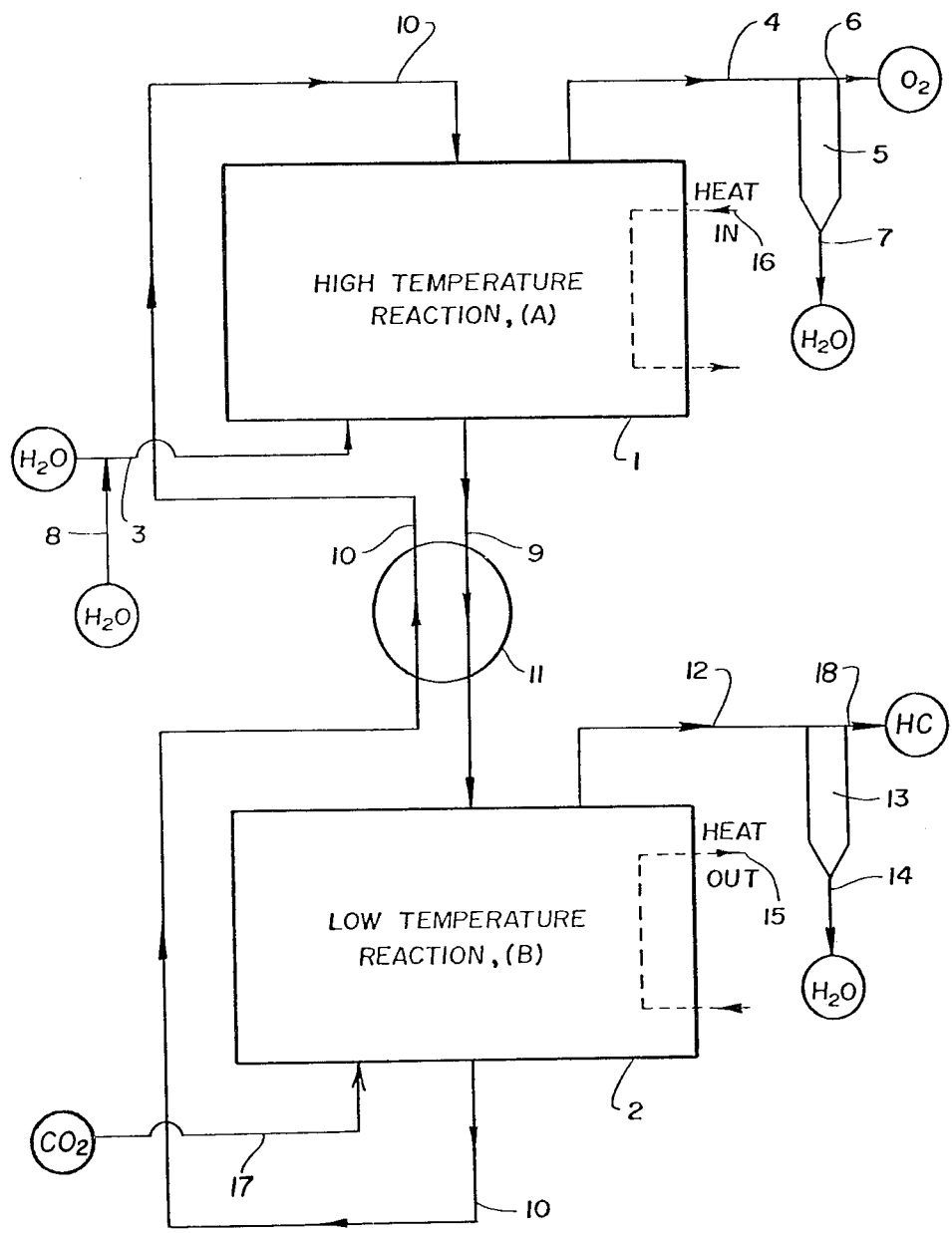

METHOD FOR PRODUCING HYDROCARBONS AND OXYGEN FROM CARBON DIOXIDE AND WATER

TECHNICAL FIELD

The subject matter of the invention is a method for producing hydrocarbons and oxygen from carbon dioxide and water.

BACKGROUND OF THE INVENTION

Man's rate of consumption of hydrocarbon fuels far exceeds nature's rate of replenishment of these fuels via the carbon cycle, fossilization and geochemistry. The consequences of the worldwide combustion of hydrocarbon fuels are an increase in the concentration of carbon dioxide in the atmosphere along with a steady diminishing of hydrocarbon fuel reserves; both to the detriment of civilization.

A process that consumes water and carbon dioxide to produce hydrocarbons and oxygen and that is driven by a non-fossil based prime energy source would help to reverse the above-described trend and thus lessen man's dependence upon fossil-based fuels. Such a process would depend on nuclear fusion or fission reactors and/or direct solar energy for prime energy input.

Direct reaction of carbon dioxide with water to produce oxygen and hydrocarbons is thermochemically unfavorable. The Gibbs free energy of reaction is large and positive at all practical temperatures and as a consequence few direct synthesis reactions have been invented to date. The situation seems made to order for a two-reaction thermochemical cycle. Such a cycle consists of two thermochemically favorable reactions that sum to equal the direct production of oxygen and hydrocarbon fuels from carbon dioxide and water. Thermochemical cycles have been the subject of much research as applied, for example, to splitting of water into hydrogen and oxygen.

The present invention entails a two-reaction thermochemical cycle for producing oxygen and hydrocarbons from carbon dioxide and water. Vaporized water is reacted endothermically at high temperature with metal cations contained within porous solid zeolite material to produce oxygen gas and reduced metal cations and protons within the solid, porous zeolite material. The reduced cation and proton containing solid zeolite material is then cooled by regenerative heat exchange to a low reaction temperature. Carbon dioxide is reacted exothermically with the cooled down, zeolite-contained, reduced metal cations and protons to produce a product gas mixture of hydrocarbons and water along with zeolite-contained metal cations oxidized to their starting oxidation state. A cyclic process is described such that the solid zeolite metal-cation-containing material cycles between the two reaction zones. For maximum thermodynamic efficiency the above-mentioned regenerative heat exchange serves to retain within the process the intrinsic heat contained by the solid zeolite material while it is cooled down and then heated up in the sequential fashion described.

Because the high temperature endothermic reaction can be driven by any source of high temperature process heat, the invented process can be driven by such non-fossil-fuel-based energy sources as nuclear fission and fusion reactors and solar collectors and concentrators.

DISCLOSURE OF THE INVENTION

Zeolites are natural and synthetic crystalline materials used extensively for ion exchange, selective adsorption, molecular sieving, and as catalyst supports, among other commercial applications. Their crystalline makeup is such that an underlying porous aluminosilicate structure is anionic and is balanced in electric charge by exchangeable cations; most frequently cations of sodium and magnesium in mineral zeolites. It is the accessibility of these charge balancing cations through the pores of the zeolite structure that makes zeolites so useful. Localization of positive and negative charge within the zeolites, along with the accessibility of the cations via the pores of the zeolite, makes these materials useful sites for oxidation-reduction reactions that involve the accessible cations. In this regard, the anionic structure of the zeolite material functions as a solid-state solvent for the cation redox reagents.

The present invention makes use of the redox properties of metal cation loaded zeolites in a two-reaction thermochemical cycle for producing hydrocarbons and oxygen from reactants carbon dioxide and water. The particular zeolite material used must have the following properties at least:

1. The zeolite structure must be hydrothermally stable to temperatures in excess of 500° C., and
2. The zeolite structure must freely admit reactant and product gas molecules. This requires zeolite pores that have minimum passage restrictions of 4 angstroms (4 times $10^{-8}$ cm) or greater in the passages that allow access to the redox reagent cations.

Not all of the over 100 known zeolite materials possess the requisite properties. Among those that meet the desired qualities, and that are candidates for use in the present invention, are zeolites offretite, L, omega, mordenite, Y, and ZSM-5. These zeolite materials have been cited in the patent literature and much of their properties have been cataloged by Donald W. Breck, "Zeolite Molecular Sieves", John Wiley & Sons.

In the present invention vaporized water under pressure is reacted endothermically with a suitable cation-loaded zeolite material at temperatures above 500° C. The redox reagent cations reside within the zeolite material and are accessible to the water vapor via the zeolite internal pore passageways. The water vapor reacts with and reduces the cations with concurrent production of protons and oxygen gas. The reduced cations and protons remain within the zeolite material and the oxygen gas is removed for storage and/or distribution. The solid product zeolite, which is in particulate form, suitable for pneumatic material transport, is removed from the oxygen-producing reaction zone, passed through a regenerative heat exchanger and cooled thereby to a temperature between 200° C. and 400° C. whereupon it passes to the low temperature exothermic reaction zone. Carbon dioxide gas is fed to the low temperature reaction zone where it reacts exothermically with the protons and reduced metal cations contained within the zeolite material and produces hydrocarbons, water vapor and oxidized metal cations in their starting oxidation state as contained within the zeolite material. The hydrocarbons and water vapor are removed from this reaction zone, the water vapor is condensed out of the product gas stream for recycling, and the hydrocarbons removed for storage and/or distribution. The product zeolite material is removed from the low temperature reaction zone, passed through the forementioned regenerative heat exchanger where it is heated to the high temperature reaction temperature, and transported to the high temperature reaction zone where the process begins again.

Because water is both a reactant in the oxygen-producing reaction and a product in the hydrocarbon-producing reaction, hydration of the zeolite material cannot be avoided at process operating pressures. On the other hand dehydration must be avoided during the process if process thermal efficiency is to be maximum. Any heat input devoted to breaking bonds of hydration cannot be recaptured and is lost to the process thus reducing process efficiency. For this reason reaction zone total pressure is kept high enough that dehydration does not occur, yet not so high that water vapor condensation occurs at subcritical water vapor temperatures within the process. Since the zeolite hydration bonds are largely ion-dipole bonds whereas water-water condensation bonds are largely much weaker hydrogen bonds, at each subcritical temperature there is a wide useful range of water vapor pressures that meet the above requirements.

Equilibrium reaction thermochemical calculations for the low temperature, exothermic, hydrocarbon-producing reaction reveal that the product gas mixture could contain such reaction intermediates as hydrogen and carbon monoxide that, in turn, can react together exothermically with appreciable conversions at the exothermic reaction temperature. Such reactions under ordinary circumstances include the well known Fischer-Tropsch synthesis reaction that yields products including high molecular weight polymethylenes, a range of olefins, a range of alcohols or polyols, aldehydes or acids as well as the lower molecular weight hydrocarbons of interest. Laboratory results reveal that the reactant mixture is altered favorably by the zeolite host material, however. Because the hydrocarbon-producing reaction takes place internal to the zeolite material the shape selective effect of the zeolite pores serves to limit the product gases largely to straight chain paraffins and olefins with carbon numbers of 9 or less.

The use of the zeolites in the present invention is fundamentally different from their use as catalyst supports such as, for example, in conventional catalytic cracking of petroleum liquids and gases. In the present invention the zeolites are used as host materials for redox reactions involving cation redox reagents whereas in conventional applications the zeolite serves as a catalyst support wherein the oxidation-reduction nature of zeolite-contained cations plays no known direct role.

BRIEF DESCRIPTION OF THE DRAWING

The appended drawing is a schematic flow diagram of the preferred embodiment of the invention and apparatus for the practice thereof.

DETAILED DESCRIPTION OF INVENTION

A high temperature endothermic reaction that consumes water vapor as a reactant and produces oxygen as a product takes place in reaction vessel 1 as shown on the FIGURE. A low temperature exothermic reaction that consumes carbon dioxide as a reactant and produces a mixture of hydrocarbons and water as products takes place in reaction vessel 2. These two chemical reactions may be written as follows (s means solid, g means gas and ze means zeolite-contained)

$$H_2O(g) + 2M^{n+}(ze) \longrightarrow 2M^{(n-1)+}(ze) + 2H^+(ze) + \tfrac{1}{2}O_2(g) \quad (A)$$

$$\left(\tfrac{x}{3x+y}\right) CO_2(g) + 2M^{(n-1)+}(ze) + 2H^+(ze) \longrightarrow \quad (B)$$

$$2M^{n+}(ze) + \left(\tfrac{1}{3x+y}\right) C_xH_{2x+2y}(g) + \left(\tfrac{2x}{3x+y}\right) H_2O(g)$$

In reaction equations (A) and (B), M denotes a metal, the cations of which are redox reagents; $n+$ and $(n-1)+$ are the higher and lower oxidation states of M, respectively, and x and y determine the carbon and hydrogen numbers of the hydrocarbon products, respectively. When the products are paraffins, $y=1$, and when the products are olefins, $y=0$.

Reaction (A) proceeds at high temperature and is endothermic, and takes place in reactor vessel 1 as shown on the FIGURE. Reaction (B) proceeds at low temperature and is exothermic, and takes place in reaction vessel 2. The temperature in the high temperature reactor vessel is at least 500° C. and as high as 950° C. whereas the temperature in the low temperature reaction vessel is from 200° C. to 400° C. The reactant bearing zeolite material circulates between these two reaction vessels.

At all times during the process the total pressure in each reaction vessel is maintained above atmospheric pressure but in no case higher than that which would cause water vapor condensation in the low temperature reaction vessel 2. The upper limit on reaction vessel total pressure is about 1500 psia and is determined by the low temperature used in the process. This temperature must be determined by a calibration procedure once the particular combination of zeolite material and metal cation reagents are selected for use in the process.

The particular zeolite material chosen must possess structural hydrothermal stability up to at least 500° C. and have pore passage dimensions that allow free passage of reactant and product gas molecules that have kinetic diameters up to 4 angstroms. Among the candidate zeolite materials are zeolites offretite, L, omega, mordenite, Y and ZSM-5, although the process is not restricted to these zeolites providing the hydrothermal stability and pore restriction requirements stated above are met.

Only a few cations are suitable for use in the invented process. Table 1 below lists metals with their higher and lower oxidation states that have been found to be suitable.

TABLE 1

| cation metal | higher oxidation state, $n+$ | lower oxidation state, $(n-1)+$ |
|---|---|---|
| Ti | 4+ | 3+ |
| V | 3+ | 2+ |
| Cr | 3+ | 2+ |
| Fe | 3+ | 2+ |
| Co | 3+ | 2+ |
| Ni | 3+ | 2+ |
| Ru | 4+ | 3+ |
| Rh | 4+ | 3+ |
| U | 4+ | 3+ |

Depending upon the zeolite host material used additional metal cations may be found to be suitable. As a general rule suitable cations in the higher oxidation state possess standard reduction potentials less positive than 3 volts, this limit serving as a useful cation screening criterion.

The preferred metal cation reagents can be introduced to the selected zeolite material by ion-exchange techniques. Following calcination at temperatures of 300° C. or higher under vacuum to clear the zeolite pores of any obstructions, the zeolite is immersed in an 0.001 to 0.1 N aqueous solution containing as a solute a suitable salt of the metal the cation of which is to be exchanged into the zeolite. After a period of hours the desired metal cation will have replaced the cations that were contained within the zeolite sample as procured (usually $H^+$, $Na^+$ and/or $Mg^{2+}$).

Water vapor is introduced via line 3 shown on the FIGURE to reaction vessel 1 which is maintained at a temperature of 500° C. or higher and a pressure above 1 atmosphere, but not above 1500 psia, where it reacts with and reduces cation $M^{n+}$ and produces cations $M^{(n-1)+}$ and $H^+$ and product gas $O_2$. High temperature process heat 16 is supplied to the reaction. A mixture of the product gas $O_2$ with $H_2O$ is fed to condenser 5 where $H_2O$ is condensed out and $O_2$ at above atmospheric pressure is removed for use or storage through line 6. Liquid water is drawn off through line 7, subsequently evaporated and fed back as a reactant through line 8.

The solid products of the oxygen producing reaction with reaction vessel 1 containing the reduced cations $M^{(N-1)+}$ and protons $H^+$ are fed to reaction vessel 2 via line 9. As these products are transported to reaction vessel 2 they are cooled down by transfer of the intrinsic heat contained therein to up-coming solid products from reaction vessel 2 being transported as reactants for reaction vessel 1 through line 10. A counter-current heat exchange takes place through heat exchanger 11. For high process thermal efficiency it is preferred that heat exchanger capacity be such that the solid reaction product of reactor vessel 1 be cooled down to below 400° C. before passing into reaction vessel 2, and that the solid reaction product of reaction vessel 2 be heated to 500° C. or higher before being fed back to reaction vessel 1.

Carbon dioxide is introduced to reaction vessel 2 at pressures above one atmosphere via line 17 where it reacts with the reduced metal cations $M^{(n-1)+}$ and protons $H^+$ to produce cations in the original oxidation state $M^{n+}$ and a gas product mixture of hydrocarbons $C_xH_{2x+2y}$ (denoted as HC in the FIGURE) and $H_2O$. The exothermic reaction heat 15 is removed at such a rate that the reactor vessel 2 temperature is maintained between 200° C. and 400° C. The precise composition of the mixture of hydrocarbons produced will depend on pressure and temperature of reactor vessel 2, rate of feed of reactant $CO_2$, the particular zeolite-cation combination used, and any catalysts contained within the zeolite host material. The mixture of hydrocarbon gases and $H_2O$ is drawn off through line 12 and fed to condensor 13 where $H_2O$ is condensed out and removed through line 14. The hydrocarbon gases are removed via line 18 for storage or distribution. The condensed $H_2O$ is evaporated and recycled as a reactant for reaction vessel 1 through line 8.

The oxidized cation-containing zeolite produced in reaction vessel 2 is transported via line 10 to reaction vessel 1 where the cycle is repeated. On its way to reaction vessel 1 the zeolite masses pass through counter flow heat exchanger 11 where they are brought up to 500° C. or greater temperature by heat transfer from the high temperature zeolite masses passing from reaction vessel 1 to reaction vessel 2 via line 9. In this way intrinsic heat is conserved within the process to the greatest possible extent.

Zeolites are manufactured and supplied in a range of particle sizes and pellet sizes and shapes. Particle sizes as small as 5–10 micron powder can be used. Such particle sizes are ideal for pneumatic transport that can be employed to transport the zeolite masses between reaction vessels. Since pellet sizes up to ⅛" by 1/16" extrudates are manufactured, the particle size can be readily adjusted to the demands of materials transport and reaction kinetics.

The limited dimensions of the pores and passages of the zeolite material will act as a steric hindrance to the formation of larger hydrocarbons and provide product gas selectively through this shape selective effect.

This invention has been described with reference to a particular embodiment but various changes and modifications may be made all within the full and intended claims which follow.

What is claimed is:

1. A method for producing hydrocarbons and oxygen from water and carbon dioxide comprising:

flowing water as steam into contact with a hydrated zeolite contained in a first reaction vessel, said zeolite that possesses thermal stability to above 500° C. and having pores large enough to pass molecules of up to 4 angstroms kinetic diameter, and containing metal cation in a high oxidation state having a standard reduction potential less positive than 3 volts, the temperature in said first reaction vessel being above 500° C. and the pressure in said reactor vessel being above 14.7 psia and sufficiently high to prevent dehydration of said zeolite, thereby to cause a reaction of said water with said zeolite which generates oxygen and which converts said zeolite to a solid product containing substantially the same number of moles of water of hydration as in said zeolite prior to said reaction and containing the metal cation in a lower oxidation state;

withdrawing oxygen from said first reaction vessel;

withdrawing said solid reaction product from said first reaction vessel and passing it through a heat exchanger and then into a second reaction vessel, the pressure in said reaction vessel being above 14.7 psia and sufficiently high to prevent dehydration of said solid reaction product, flowing carbon dioxide into contact with said solid reaction product, the temperature in said second reaction vessel being below 400° C. and being at least 200° C. less than the temperature in said first reaction vessel, thereby to cause a reaction of said carbon dioxide with said solid reaction product which produces a mixture of hydrocarbons and water and which converts said solid reaction product to said zeolite containing the metal cation in its high oxidation state;

withdrawing the mixture of hydrocarbons and water from said second reaction vessel; and withdrawing the zeolite from said second reaction vessel and passing it through said heat exchanger into said first reaction vessel, said zeolite from the second reaction vessel being heated in said heat exchanger from said solid reactant product passing through said heat exchanger from said first reaction vessel.

2. A method as set forth in claim 1 wherein in said first reaction vessel the temperature is from 500° C. to 950° C. and the pressure is from 14.7 psia to 1500 psia and wherein said second reaction vessel the temperature is from 200° C. to 400° C. and the pressure is from 14.7 psia to 1200 psia.

3. A method as set forth in claim 1 wherein said zeolite and said solid reaction product are in finely divided form and wherein the water and the carbon dioxide are continuously flowed into said first and second reactor vessels, respectively, the oxygen and hydrocarbon and water mixture are continuously withdrawn from said first and second reactor vessels, respectively, solid reaction product from said first reactor vessel is continuously withdrawn and passed through said heat exchanger and into said second reaction vessel and the zeolite from said second reaction vessel is continuously withdrawn and passed through said heat exchanger and into said first reaction vessel.

4. A method as set forth in claim 1 wherein, during passage through said heat exchanger, said solid reaction product is cooled to below 400° C. and said zeolite from said second reaction vessel is heated to above 500° C.

5. A method as set forth in claim 1, 2, 3 or 4 wherein the cation metal of said zeolite is selected from the group Ti, V, Cr, Fe, Co, Ni, Ru, Rh, and U.

6. A method as set forth in claim 1, 2, 3 or 4 wherein the cation metal of said zeolite is vanadium.

7. A method as set forth in claim 1, 2, 3 or 4 wherein the cation metal of said zeolite is ruthenium.

8. A method as set forth in claim 1, 2, 3 or 4 wherein the cation metal of said zeolite is titanium.

9. A method as set forth in claim 1, 2, 3 or 4 wherein the cation metal of said zeolite is cobalt.

10. A method as set forth in claim 1, 2, 3 or 4 wherein the cation metal of said zeolite is uranium.

* * * * *